United States Patent [19]

Anderson

[11] Patent Number: 4,751,235
[45] Date of Patent: Jun. 14, 1988

[54] ANTI-ATHEROSCLEROTIC INDOLIZINE DERIVATIVES

[75] Inventor: Paul L. Anderson, Randolph, N.J.

[73] Assignee: Sandoz Pharm. Corp., East Hanover, N.J.

[21] Appl. No.: 945,750

[22] Filed: Dec. 23, 1986

[51] Int. Cl.$^4$ .................. A61K 31/435; C07D 471/04
[52] U.S. Cl. ..................................... 514/299; 546/112
[58] Field of Search ......................... 546/112; 514/299

[56] References Cited

U.S. PATENT DOCUMENTS

| | | | |
|---|---|---|---|
| 4,248,889 | 2/1981 | Oka et al. | 424/308 |
| 4,255,444 | 3/1981 | Oka et al. | 424/279 |
| 4,375,475 | 3/1983 | Willard et al. | 549/292 |
| 4,474,971 | 10/1984 | Wareing | 549/214 |
| 4,520,026 | 5/1985 | Rosseels et al. | 546/112 |

FOREIGN PATENT DOCUMENTS

| | | |
|---|---|---|
| 8402131 | 6/1984 | PCT Int'l Appl. |
| 8402903 | 8/1984 | PCT Int'l Appl. |
| 8600307 | 1/1986 | PCT Int'l Appl. |
| 8603488 | 6/1986 | PCT Int'l Appl. |

Primary Examiner—Richard A. Schwartz
Assistant Examiner—Bernard I. Dentz
Attorney, Agent, or Firm—Gerald D. Sharkin; Richard E. Vila; Melvyn M. Kassenoff

[57] ABSTRACT 7-(indolizin-2-yl)hept-6-enoic acids of the formula I:

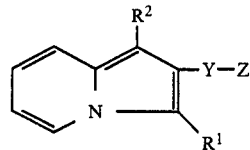

wherein each of $R^1$ and $R^2$ is, independently, H, alkyl, cycloalkyl, aralkyl or aryl, Y is —CH=CH—, or —CH$_2$—CH$_2$—; and Z is CH—CH$_2$—CH—CH$_2$COOR$^8$
　　｜　　　　｜
　　OH　　　OH in which $R^8$ is H, an ester residue or cation; or the lactone thereof. The compounds are useful as hypocholesteremic agents.

20 Claims, No Drawings

ANTI-ATHEROSCLEROTIC INDOLIZINE DERIVATIVES

This invention pertains to organic compounds, and more particularly to 7-(indolizine-2-yl)-hept-6-enoic acid derivatives as well as to the use of such compounds and pharmaceutical compositions containing such compounds, as well as to intermediates and methods of preparation.

The final compounds involved in the invention may be conveniently represented by formula I:

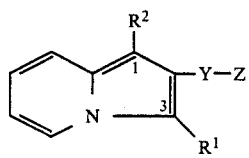

I wherein each of $R^1$ and $R^2$ is, independently:

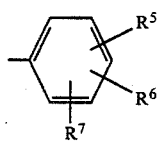

(a)

(b) hydrogen or a primary or secondary $C_{1-6}$alkyl not containing an asymmetric carbon atom, (c) $C_{3-6}$cycloalkyl or (d) phenyl—$(CH_2)_m$—,
wherein $R^5$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy;
$R^6$ is hydrogen, $C_{1-3}$alkyl, $C_{1-3}$alkoxy, fluoro or chloro;
$R^7$ is hydrogen, $C_{1-2}$alkyl, $C_{1-2}$alkoxy, fluoro or chloro;
m is 1, 2 or 3;

Y is (a) 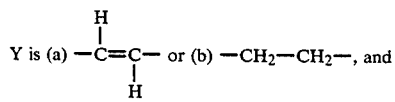 or (b) —$CH_2$—$CH_2$—, and

Z is 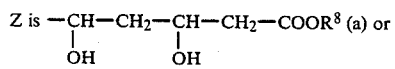 (a) or

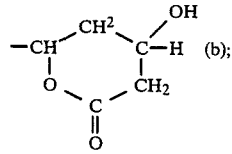 (b);

in which $R^8$ is hydrogen, $R^9$ or M, wherein
$R^9$ is a physiologically acceptable and hydrolyzable ester group, and
M is a pharmaceutically acceptable cation Compounds I may be viewed as consisting of various sub-classes depending upon the definition of their variable portions. Compounds I may be of the following subclasses depending on the nature of Z;

| Designation: | Z = | Nature |
|---|---|---|
| Compounds I1 | type (a); $R^8 = R^9$ | ester |
| Compounds I2 | type (a); | salt |
| Compounds I3 | type (a); $R^8 = M$ | free acid |
| Compounds I4 | $R^8 = H$, type (b) | lactone |

A preferred type of Compounds I is designated I' where Y=(a) and one of $R^1$ and $R^2$ is H or alkyl, especially methyl or isopropyl, and the other is an aryl group i.e. (a), especially p-fluorophenyl, phenyl or 3,5-dimethylphenyl, and particularly p-fluorophenyl.

When $R^8$ is $R^9$, it is preferably ethyl, and when it is M, it is preferably sodium, potassium, magnesium or calcium, especially sodium.

By the term "physiologically acceptable and hydrolyzable ester group" is meant a group which, together with the —COO— radical to which it is attached, forms an ester group which is physiologically acceptable and hydrolyzable under physiological conditions to yield a compound of Formula I wherein $R^8$ is hydrogen and an alcohol which itself is physiologically acceptable, i.e., non-toxic at the desired dosage level, and which, preferably, is free of centers of asymmetry. Examples of such groups are $C_{1-3}$alkyl, n-butyl, i-butyl, t-butyl and benzyl, collectively referred to as $R^{9'}$.

A particular sublcass of Compounds I is Compounds I1'' in which $R^8$ is $R^{9'''}$, i.e. $C_{1-4}$ primary alkyl, especially ethyl.

Compounds I may further be viewed as two sub-classes depending on the nature of the group Y, i.e. Ia where Y=(a) and Ib where Y=(b), the former being preferred.

As is well known in the art, ester and salt forms of an organic acid are interconvertible. Hence, where an ester form (here I1) is prepared, it can then be saponified to its corresponding salt (I2) which can be neutralized to the free acid form (I3), which can be cyclized to the corresponding lactone (I4), and the reverse; all by adapting conventional processes. Accordingly, preparation of an ester I1 where $R^8$ is $R^{9'''}$, i.e. I1'', provides a compound of the invention, as well as a source of the corresponding other forms of Compounds I.

Compounds I1a'' (i.e. Compounds I (in which Y=(a), Z=(a) and $R^8=R^{9'''}$), are obtainable by a multi-step procedure which may conveniently be represented by Reaction Schemes A and B below, in which $R^1$, $R^2$ and $R^{9'''}$ are as defined above, $R^{16}$ and $R^{17}$, are, independently, alkyl ($C_{1-3}$) preferably ethyl, $R^{20}$ is a primary or secondary $C_2$-$C_4$alkyl, eg ethyl; and $R^{21}$ is allyl or $C_1$-$C_4$alkyl, preferably not tertiary, e.g. methyl, X is Cl, Br or I, and Q has the structure:

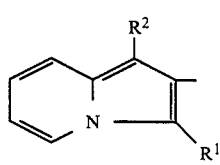

Q in which $R^1$ and $R^2$ are as defined above.

REACTION SCHEME A

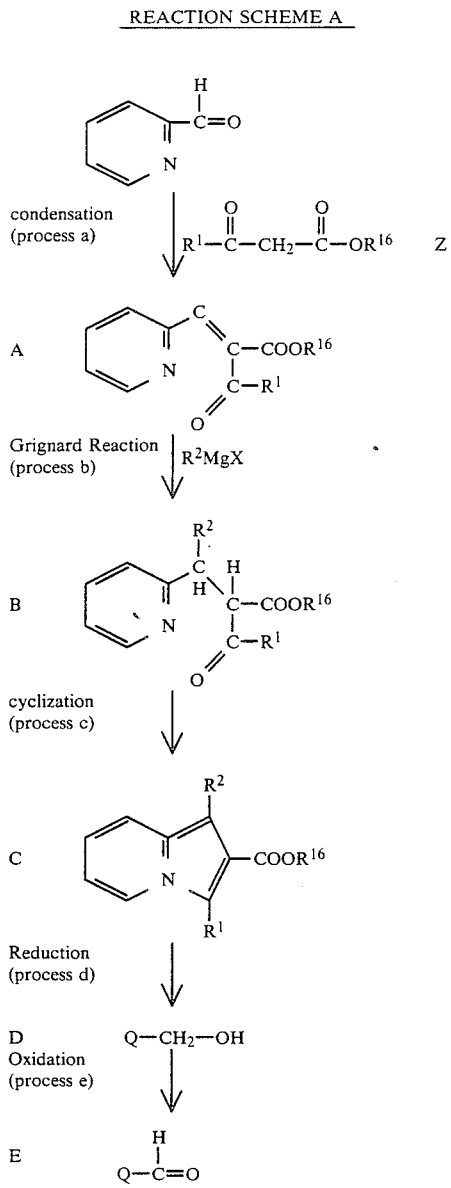

REACTION SCHEME B

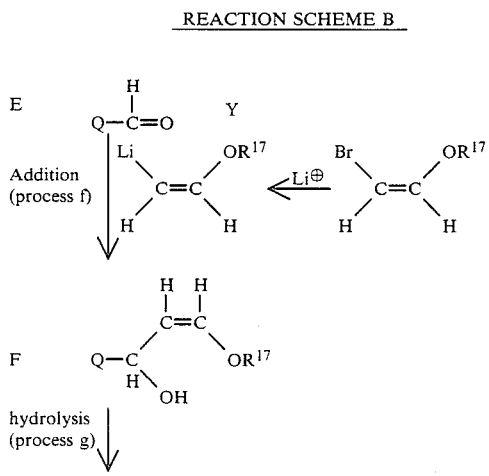

-continued
REACTION SCHEME B

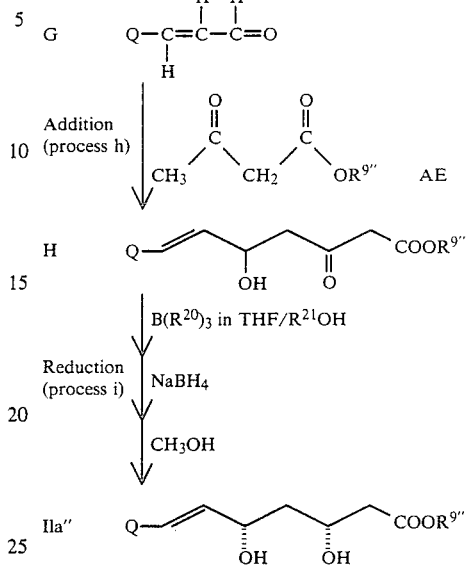

Individually, each of the above described reactions is analogous to reactions, known in the art, except for process (i), and may be carried out in the conventional manner, unless indicated otherwise.

The parameters applicable to the processes illustrated in the Reaction Schemes, above, are listed in the following tables, in which general parameters are described with preferences as examples. In processes in which a medium is employed, it is understood that the medium is an inert solvent under the reaction conditions and is essentially anhydrous, i.e. moisture-free, if dry, i.e. essentially anhydrous conditions are called for. Where anhydrous conditions are called for, it is preferred that such reaction be carried out in an inert atmosphere eg under dry nitrogen gas.

In the tables, Q indicates an alkali metal salt usually used in situ, and [ ] indicates an adduct or complex reaction product which is reacted in a subsequent quenching step, usually quenched to hydrolyze or decompose it. Where a quenching step is employed, water is used, but often as an aqueous solution, e.g. saturated aqueous $NH_4Cl$. LAH=lithium aluminum hydride; ether=diethyl ether; RT=20° to 30° C., THF=tetrahydrofuran and PTS=p-toluenesulfonic acid. All temperatures are in degrees centigrade; these abbreviations etc., also applying to the Examples hereinafter presented.

Process (i) is novel and is not claimed as part of this invention. In an alternative method of carrying out process (i), in place of a trialkyl borane reagent there may be used an equivalent amount of a monoalkoxy dialkyl borane of the formula Gk:

$$R^{22}O—B—(R^{20})_2 \qquad Gk$$

in which $R^{20}$ and $R^{21}$ are defined hereinafter in the tables, and $R^{22}$ is allyl or a lower alkyl having from 1 to 4 carbon atoms, preferably not tertiary. $R^{20}$, $R^{21}$ and $R^{22}$ may be the same, but need not be. Preparation of Compounds Gk are described by Koster et al, Ann., 1975, 352. $R^{21}$ and $R^{22}$ are preferably methyl.

TABLE A

| | |
|---|---|
| Process (a): | Condensation |
| Reactant(s): | 2-pyridyl-CHO + Z → A |
| Medium: | Neat |
| Temperature: | 20° to 80° C., eg RT, then 80° C. |
| Conditions: | Catalytic amount of piperidine; dry. |
| Process (b): | Grignard Reaction |
| Reactant(s): | (1) A + $R^2$MgX → [ ]; |
| | (2) quench, eg, aq. $NH_4Cl$ → B. |
| Medium: | Cyclic ether, eg THF, with Grignard reagent in ether. |
| Temperature: | (1) −70 to RT (add Cu(1)I at about 0°). |
| Conditions: | Dry, cat. amt. of Cu(1)I. |
| Process (c): | Cyclization |
| Reactant(s): | (1) B + Acetic Acid Anhydride; → [ ]; |
| | (2) quench (water) → C |
| Medium: | Excess AAA. |
| Temperature: | Reflux. |
| Conditions: | — |
| Process (d): | Ester Reduction |
| Reactant(s): | (1) C + LAH → [ ]; |
| | (2) Destroy excess LAH with ethyl acetate, then quench with ice-water → D. |
| Medium: | THF |
| Temperature: | (1) −5° C. to 30° C., eg add LAH at 0° C. to raise to RT; |
| | (2) Cold. eg ice-water bath. |
| Conditions: | (1) dry; (2) add ethylacetate cautiously. |
| Process (e): | Oxidation to aldehyde |
| Reactant(s): | D + $MnO_2$ → E |
| Medium: | Inert hydrocarbon, eg toluene. |
| Temperature: | 20 to 140°, eg reflux conditions. |
| Conditions: | Dry |
| Process (f): | Addition of olefinic unit |
| Reactant(s): | (1) BrCH=CH—$OR^{17}$, eg $R^{17}$ = ethyl, + $Li^\oplus$ source, eg t-butyl lithium → Y |
| | (2) Y + E → [ ]. |
| | (3) [ ] + quench, eg ice-water or sat. aq. $NH_4Cl$, → F |
| Medium: | (1) Cyclic ether, eg THF; (1) = (2). |
| Temperature: | (1) −40 to −100° C., eg about −70°; (1) = (2); (3) 0° C. to RT. |
| Conditions: | Essentially anhydrous for (1) + (2). |
| Process (g): | Hydrolysis |
| Reactant(s): | F + aq. PTS → G |
| Medium: | Cyclic ether, eg THF + water in ratio of about 4:1. |
| Temperature: | RT |
| Conditions: | — |
| Process (h): | Addition via dianion (3 stages) |
| Reactant(s): | (1) AE, eg ethyl acetate, + 2 equivalents of alkali cation, eg 2 LDA → Q. |
| | (2) Q + G → [ ]. |
| | (3) [ ] + quench, eg ice-water or saturated aqueous $NH_4Cl$ → H. |
| Medium: | (1) Cyclic ether, eg THF. (1) = (2) = (3). |
| Temperature: | (1) −60 to +5°, eg 0 to +5°. |
| | (2) −80° to −20°, eg −75° to −60°. |
| | (3) 0° to R.T. |
| Conditions: | Dry for (1) + (2). |
| Process (i): | Reduction (3 stages) |
| Reactant(s): | (1) H + $B(R^{20})_3$ eg $R^{20}$ = ethyl, in a ratio of about 1:1.02 to 1.3 → [ ]. |
| | (2) $NaBH_4$ + [ ] → [ ]'. |
| | (3) [ ]' + $H^\oplus$, eg acetic acid, → IIa'' |
| Medium: | (1) THF/$R^{21}$OH, eg, $R^{21}$ = methyl; ratio = 3 to 6:1, eg 3-4:1. |
| | (1) = (2) = (3). |
| Temperature: | (1) R.T. |
| | (2) −100 to −40°, eg −75°. |
| | (3) −100 to −40°, eg −75°, then to R.T. |
| Conditions: | Dry for (1) + (2). Optionally, air may be bubbled through reaction mixture in (1). |

Analogs of Compounds IIa'' in which Y is of type (b) i.e. Compounds IIb'' are conveniently obtained by a two-step procedure, by first saturating the olefinic unit of a corresponding compound H (process j) to yield a saturated analog of a compound H, i.e. a compound Hb, and then reducing such compound in a manner analogous to process (i).

Process (j) may be carried out in the conventional manner for hydrogenating an ethylenically unsaturated bond, under conditions that do not alter the remainder of the compounds; for example at about 20° to 40° C., e.g. R.T. under a pressure of about 40 to 50 p.s.i. of hydrogen gas in the presence of a hydrogenation catalyst e.g., 5% palladium on charcoal or 5% rhodium on charcoal, in an inert medium, e.g. a lower alkanol, such as ethanol. alternatively a compound IIa'' can be reduced by the procedure of process (j) to obtain its corresponding saturated analog (a compound IIb''). As described above, such esters can be converted by known means to their corresponding free acid, salt and lactone forms.

The products described herein may be recovered and refined, where such is desired, by conventional means, such as by crystallization, distillation or chromatographic techniques such as column or thin layer chromatography, (TLC) e.g., silica gel column chromatography. Where appropriate, intermediates can be employed directly in a subsequent reaction.

Reagents and starting materials employed in the above-described processes, e.g. 2-pyridine carboxaldehyde and Y, Z, AE and $B(R^{20})_3$, are either known and may be obtained as described in the literature, or where not known may be prepared by methods reported in the literature for the preparation of known analogues. Some are commercially available.

UTILITY STATEMENT

The compounds of Formula I are competitive inhibitors of 3-hydroxy-3-methylglutaryl coenzyme A (HMG-CoA) reductase, the rate limiting enzyme in cholesterol biosynthesis, and, therefore, they are inhibitors of cholesterol biosynthesis. Consequently, they are useful for lowering the blood cholesterol level in animals, e.g., mammals, especially larger primates such as humans, and, therefore, as hypolipoproteinemic and anti-atherosclerotic agents. The biological activity of the compounds of Formula I may be demonstrated in the following two tests:

Test A. In Vitro Microsomal Assay of HMG-CoA Reductase Inhibition:

This test is known and is carried out as described on pages 59-60 of application Ser. No. 06/741,903 (filed June 6, 1985) and on page 30 of World (PCT) Published Patent Application No. 84/02131 both of which are hereby incorporated by reference as if set forth herein in their entirety. The concentration of the test substance (compound of Formula I) in the assay system is 0.0005-2,000 μmolar. The obtained $IC_{50}$ is the concentration of the test substance in the assay system observed or calculated to produce a 50% inhibition of HMG-CoA reductase activity.

Test B. In Vivo Cholesterol Biosynthesis Inhibition Test:

This test is also known and is carried out as described on pages 60-61 of said application Ser. No. 06/741,903 and on page 33 of World (PCT) Published Patent Application No. 84/02131, both of which are hereby incorporated by reference as if set forth herein in their entirety. In this test the rats are orally administered the test substance (compound of Formula I) at a dose of 0.025-200 mg/kg. body weight. The obtained $ED_{50}$ is the dose of the test substance observed or calculated to produce a 50% inhibition of 3 β-hydroxysterol synthesis.

In Test A, tested compounds of Formula I had $IC_{50}$'s of about 0.006 to over 10 μmolar whereas that of Compactin was 1.01 μmolar and that of Mevinolin was 0.14 μmolar. The preferred compound of this application, that of Example 2, had an $IC_{50}$ of 0.011 μmolar. In Test B, the compound of Example 1 had an $ED_{50}$ of 0.05 mg/kg. whereas that of Compactin was 3.5 mg/kg. and that of Mevinolin was 0.41 mg/kg.

Since they inhibit cholesterol biosynthesis, the compounds of Formula I (including those of each subgroup thereof) are useful for lowering the blood cholesterol level in animals, eg., mammals, especially larger primates, in particular humans, and, therefore, as hypolipoproteinemic and anti-atherosclerotic agents.

The precise dosage of the compound of Formula I to be employed for inhibitng cholesterol biosynthesis depends upon several factors including the host, the nature and the severity of the condition being treated, and the mode of administration and the particular active substance (compound of Formula I) employed. However, in general, suitable oral daily dosages of the compounds of Formula I for the satisfactory inhibition or reduction of cholesterol biosynthesis (i.e., the satisfactory reduction of blood cholesterol level and satisfactory treatment of hyperlipoproteinemia and atherosclerosis) are indicated by the test data to be 0.025–100 mg/kg. body weight, e.g., 0.025–5 mg/kg. body weight for the more active compounds. For most larger primates such as humans, a suitable oral daily dosage is indicated to be 0.1–2,000 mg., e.g., 2–140 mg. for the more active compounds. The daily dosage of the compound of Example 2, is indicated to be from about 2 to 140 mg., preferably from about 2 to 20 mg., for most larger primates such as humans. For administration by injection, a dosage somewhat lower than would be used for oral administration of the same active substance to the same host having the same condition is usually employed. However, the above dosages are also typically used for I.V. administration.

The daily dosage may be administered in a single dose but more typically is administered in two to four equal portions, typical doses being 0.5 to 1000 mg. Often, a small dosage is administered initially, and the dosage is gradually increased until the optimal dosage for the host under treatment is determined.

A typical dosage unit for oral administration may contain 0.5 to 500 e.g. 0.5 to 10 mg of a compound of Formula I.

The compounds of Formula I may be formulated into conventional pharmaceutical compositions and administered by any conventional mode of administration, in particular enterally, e.g., in the form of capsules or tablets, or parenterally, e.g., in the form of sterile injectable solutions or suspensions. The pharmaceutical compositions comprise a compound of Formula I and at least one pharmaceutically acceptable solid or liquid carrier (or diluent). They may be formulated in conventional manner. The compounds of each subgroup thereof may likewise be formulated into such pharmaceutical compositions and administered by such routes.

The compounds of Formula I (including those of each subgroup thereof) may be formulated into such pharmaceutical compositions containing an amount of the active substance that is effective for inhibiting cholesterol biosynthesis in unit dosage form and such compositions comprising at least one solid pharmaceutically acceptable carrier.

A representative formulation suitable for encapsulation in a hard gelatin capsule by conventional techniques is:

Compound of Formula I, e.g., the compound of

| Compound of Formula I, e.g., the compound of | |
|---|---|
| Example 2 | 1 mg. |
| Corn starch | 248 mg. |
| Magnesium stearate | 1 mg. |

As is self-evident to those in the art, each compound of formula I (and every sub-scope and species thereof) has at least two centers of asymmetry (e.g. the two carbon atoms bearing the hydroxy groups in the structure when Z=a) and the carbon atom bearing the hydroxy group and the carbon atom having the free valence in the structure when Z=b), and these lead (e.g. with two centers) to four stereoisomeric forms (enantiomers) of each compound (two racemates or pairs of diastereoisomers). The preferred compounds have only two such centers of asymmetry and these four stereoisomers may be designated as the R,R; R,S; S,R; and S,S enantiomers, all four stereoisomers being within the scope of this invention.

The preferred stereoisomers of the compounds of formula I having only two centers of asymmetry wherein Y is a) and Z is a) are the 3R,5S and 3R,5R isomers and the racemate of which each is a constituent, i.e., the 3R,5S-3S,5R (erythro) and 3R,5R-3S,5S (threo) racemates, with the 3R,5S isomer and the racemate of which it is a constituent being more preferred and the 3R,5S isomer being most preferred.

The preferred stereoisomers of the compounds of formula I having only two centers of asymmetry wherein Y is (b) and Z is (a) are the 3R,5R and 3R,5S isomers and the racemate of which each is a constituent, i.e., the 3R,5R-3S,5S (erythro) and 3R,5S-3S,5R (threo) racemates, with the 3R,5R isomer and the racemate of which it is a constituent being more preferred and the 3R,5R isomer being most preferred.

The preferred stereoisomers of the compounds of formula I having only two centers of asymmetry wherein Y is (a) and Z is (b) are the 4R,6S and 4R,6R isomers and the racemate of which each is a constituent, i.e., the 4R,6S-4S,6R (trans lactone) and 4R,6R-4S,6S (cis lactone) racemates, with the 4R,6S isomer and the racemate of which it is a constituent being more preferred and the 4R,6S isomer being most preferred.

The preferred stereoisomers of the compounds of formula I having only two centers of asymmetry wherein Y is (b) and Z is (b) are the 4R,6R and 4R,6S isomers and the racemate of which each is a constituent, i.e., the 4R,6R-4S,6S (trans lactone) and 4R,6S-4S,6R (cis lactone) racemates, with the 4R,6R isomer and the racemate of which it is a constituent being more preferred and the 4R,6R isomer being most preferred.

The preferences set forth in the preceding four paragraphs also apply to the compounds of formula I having more than two centers of asymmetry and represent the preferred configurations of the indicated positions.

Compounds I having one or more of the following characteristics are preferred:
(a) Y=(a);
(b) Z=(a);
(c) when Z=a, $R^8$=M, especially sodium;

(d) and when Y=(a) and Z=(a) the optically active isomer of the 3R,5S form.

Reagents and reaction products which are mixtures of stereoisomers (cis, trans and optical) can be separated by conventional means at whatever stage of synthesis is appropriate. Such methods include re-crystallization, chromatography, e.g. HPLC, formation of esters with optically pure acids and alcohols or of amides and salts with subsequent reconversion with retention of optical purity. For example diastereoisomeric (−)-α-naphthyl-phenylmethylsilyl derivatives of a lactone type end product of formula I may be separated by conventional means, e.g. as disclosed in U.S. Pat. No. 4,613,610.

The following examples are illustrative of the invention. All temperatures are centigrade and room temperature (R.T.) is 20° to 30° C., unless indicated otherwise.

Unless indicated otherwise, evaporations are done under reduced pressure, drying of extracts is done over anhydrous sodium sulfate, all ratios of liquid mixtures are volume to volume, and moisture-free solvents and dry nitrogen atmosphere are employed for all reactions which are indicated to be carried out under essentially anhydrous conditions.

EXAMPLE 1

7-[3-(4-fluorophenyl)-1-(1-methylethyl)-2-indolizinyl]-3,5,-dihydroxy-6-heptenoic acid, ethyl ester (trans) (a Compound II)

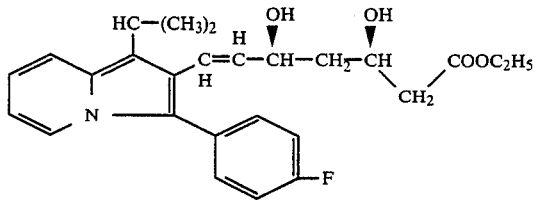

Step 1, 2-(4'-fluorobenzoyl)3-(2-pyridinyl)propenoic acid, methyl ester (a Compound A).

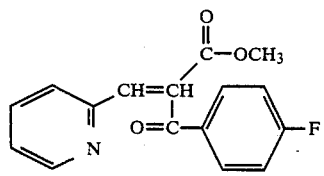

30 g (0.15 M) of methyl 4-fluorobenzoyl acetate are added to 16.05 g (0.15 M) of 2-pyridine carboxaldehyde. 4 drops of piperidine are then added, and the mixture stirred at R.T. for about 16 hours. The mixture is then heated at about 80° for about 5 hours during which the mixture thickens markedly, yielding crude title product of this step. The mixture is then cooled and solidifies on standing. The solids are broken up, washed with methanol, then triurated with hot methanol and the solution evaporated to dryness, then crystallized from petroleum ether-methanol (50:50), yielding the refined title product of this step for use in Step 2, below.

Step 2, 2-(4-fluorobenzoyl)-3-(1-methylethyl)-3-(2-pyridinyl)propanoic acid, methyl ester (a Compound B).

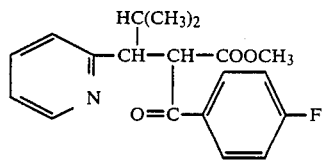

1.89 ml of 2 M (0.0035 M) isopropyl magnesium chloride (in diethyl ether) is added to 25 ml dry THF. At 0°, 40 mg of cuprous iodide (Cu(1)I) 0.17 mM is added and the mixture cooled to −70°. One gram of the 2-propenoic acid ester of Step 1 in 8 ml of dry THF is added rapidly. The temperature of the mixture is raised to −50°, and maintained and then maintained for one-half hour at −50° to −70°. There is then added 40 mg of cuprous iodide and the mixture is allowed to slowly warm to R.T. and stirred for about 16 hours.

Saturated aqueous ammonium chloride is then added to the mixture, and crude product of this step extracted by ethyl acetate. The extracts are combined and evaporated to obtain crude product which is used as such in the next step (step 3).

Step 3, 3-(4-fluorophenyl)-1-(1-methylethyl)-2-indolizinecarboxylic acid, methyl ester (a Compound C).

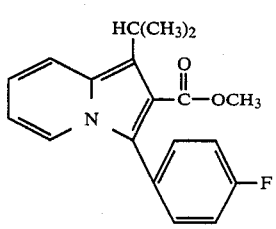

23 g of the crude 2-pyridinepropanoic acid ester product of Step 2, above, is added to 300 ml of acetic acid anhydride. The mixture is slowly heated to reflux and gently refluxed for 3.5 hours. The mixture is then added to ice-water and 0.5 liter of 2N NaOH and extracted with ethyl acetate. The organic phase is dried and evaporated to obtain crude title product of this step. The product is refined by chromatographing through silica gel (eluting with ethyl acetate/hexane (20:80). The fractions are combined and product recovered by crystallizing (mp 139°–142°).

Step 4, 3-(4-fluorophenyl)-1-(1-methylethyl)-2-indolizinemethanol (may also be called 3-(4-fluorophenyl)-1-isopropyl-2-hydroxymethylindolizine) (a Compound D).

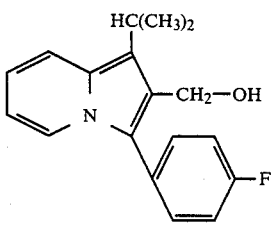

5.1g (0.016 M) of the indolizine product of Step 3, above, in 300 ml of dry THF is cooled to 0°. 1.8 g of LAH is slowly added over a 1 hour period. With stirring, the temperature of the mixture is to rise to room temperature. The mixture is then cooled (in a ice-water bath) and ethyl acetate added dropwise to decompose unreacted LAH. Ice-water is then slowly added, and the product extracted with ethyl acetate. The extracts are combined, dried and evaporated to dryness to obtain the title product of this step (as a semi-solid).

Step 5, 3-(4-fluorophenyl)-1-(1-methylethyl)-2-indolizinecarboxaldehyde (a compound E).

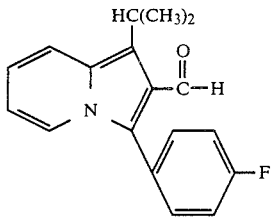

4.7g (0.17 M) of the alcohol product of Step 4, above, is added to 250 ml of toluene. 20g of manganese dioxide are then added, and the mixture is heated slowly to reflux. When TLC indicates that no starting material remain (about 1 hour), the mixture is filtered through celite, washing with toluene then methylene chloride. The filtrate (organic phase containing the product) is evaporated to dryness to recover the title aldehyde product of this step.

Step 6, 1-(2-ethoxyethenyl)-[3-(4-fluorophenyl)-1-(1-methylethyl)-2-indolizine]methanol (a Compound F).

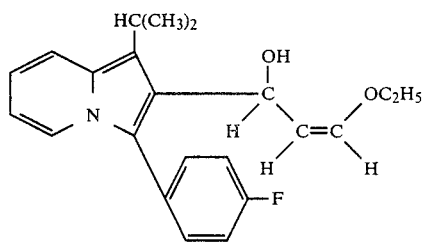

First, a reagent (Y) is prepared by adding 0.815 g (5.4 mM) of cis-1-bromo-2-ethoxyethylene to 51 ml of dry THF; the mixture cooled to −70°, and 6.47 ml of 1.7 M t.-butyl lithium (0.011 M) added dropwise. The resulting mixture is stirred for 1 hour at −70°.

To the above-described reagent solution is added 1.4 g (4.9 mM) of the aldehyde product of Step 5, above, in a minimum volume of dry THF. The resulting mixture is stirred, at −70°, for 2 hours (until none or merely a trace of, starting material remains).

The mixture is added to ice-water, and extracted with ethyl acetate, the extracts combined, dried and evaporated to obtain as a residue crude title olefinic product of this step; which is used directly in Step 7, below.

Step 7, 3-[3-(4-fluorophenyl)-1-(1-methylethyl)-2-indolizinyl]-2-propenal (trans; a Compound G).

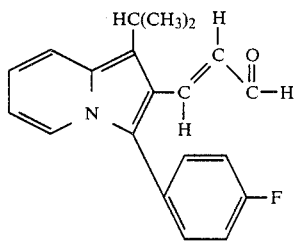

The olefinic crude product of Step 6, above, is added to a mixture of 160 ml of THF +40 ml water and one gram of p-toluene sulfonic acid added. The resultant mixture is stirred for about 16 hours at R.T. The mixture is added to water and extracted with ethyl acetate. The combined extracts are dried, then evaporated to dryness then held for 2 hours under high vacuum. The product is then flash chromatographed.

Step 8, 7-[3-(4-fluorophenyl)-1-(1-methylethyl)-2-indolizinyl]-5-hydroxy-3-oxo-6-heptenoic acid, ethyl ester (trans).

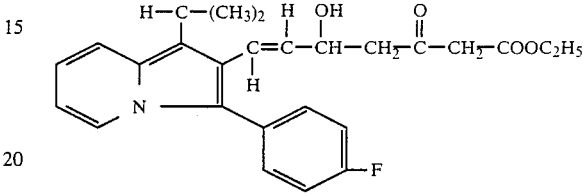

Reagent (Q) is first prepared by adding under a dry nitrogen atmosphere 1.13g (11.2 mM) of diisopropylamine to 50 ml of dry THF; the mixture cooled to 0° to 5°, and 7.22 (11.2 mM) ml of 1.55 M n-butyl lithium (in hexane) is added dropwise thereto. The mixture is maintained at 0° to 5° for 15 minutes, then 0.728 g (5.6 mM) of ethyl acetoacetate (distilled) is added dropwise, and the mixture stirred at 0° to 5° for 1 hour.

The thus-prepared reagent ( ) mixture is then cooled to −60° and 0.8721 g (2.8 mM) of the olefinic aldehyde product of Step 7, above, in a minimum volume of dry THF is added thereto and the mixture stirred at about −60° to −75° for 1 hour.

The reaction mixture is allowed to warm, ice-water added, and the mixture extracted with ethyl acetate. The combined extracts are dried, then evaporated to dryness to yield the crude title product of this step. This product is then flash distilled using ethyl acetate-methylene chloride (5:95 v/v) to obtain refined product (as a thick dark oil) for use in Step 9, below.

Step 9, 7-[3-(4-fluorophenyl)-1-(1-methylethyl)-2-indolizinyl]-3,5,-dihydroxy-6-heptenoic acid, ethyl ester (trans).

437 mg (1 mM) of the keto-ester product of Step 8, above, is mixed with 60 ml dry THF and then 15 ml of dry methanol. At R.T., 1.3 ml of 1 M triethylborane in THF are added. Then is added 8 ml of air. The mixture is stirred (at R.T.) for 2 hours.

The mixture is then cooled to −72°, 56 mg of sodium borohydride added and the mixture stirred for 3 hours at −72°. 30 mg additional sodium borohydride is added and the mixture stirred for 1 more hour at −72°. One ml of acetic acid is then added dropwise. The temperature of the mixture is allowed to rise to R.T. The mixture is then held at R.T. for 16 hours. 20 ml of 10% aqueous sodium bicarbonate solution is then added. Additional water is added and the product of this example is extracted with ethyl acetate. The combined extracts are dried and then evaporated to yield crude title product of this example. The product may be refined by chromatographing on prep. plates, eluting with methanol/methylene chloride (5:95), as an oil; the erythro isomer predominating about 95:5.

EXAMPLE 2

7-[3-(4-fluorophenyl)-1-(1-methylethyl)-2-indolizinyl]-3,5,-dihydroxy-6-heptenoic acid, sodium salt (trans)

To 14 ml of absolute ethanol is added 147.9 mg of 7-[3-(4-fluorophenyl)-1-(1-methylethyl)-2-indolizinyl]-3,5,-dihydroxy-6-heptenoic acid, ethyl ester (Example 1, above), and the solution cooled to +5°. There is then added thereto, dropwise 0.34 ml of 1 N aq. sodium hydroxide (0.34 mM). The mixture is stirred for 2 hours while the temperature is allowed to rise. The mixture is evaporated to dryness, to obtain a residue, which is then held under high vacuum for 2 hours at 40°. Methylene chloride is added, the mixture warmed, filtered, cold ether is added dropwise, causing solids to precipitate. The solids are collected on by filtration, washed with ether, then dried at 40° under high vacuum to yield the title product, which decomposes at above 230°, the erythro isomer predominating about 9:1.

Adapting the procedure of Examples 1 and 2, the following compounds I1 and I2 are obtained in which Y=a) and Z=a), (the erythro isomer predominating about 9:1); (in the table Et=ethyl, ip=isopropyl, i.e. 1-methylethyl, and ph=phenyl.

| Example No. | $R^1$ | $R^2$ | $R^8$ | Form | |
|---|---|---|---|---|---|
| 3 | 4-F-ph | H | Et | Oil | >200° C. |
| 4 | 4-F-ph | H | Na | solid decomp. | |
| 5 | ip | 4-F-ph | Et | oil | |
| 6 | ip | 4-F-ph | Na | Solid decomp. | >220° C. |

What is claimed is:

1. A compound of formula I:

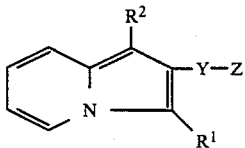

wherein each of $R^1$ and $R^2$ is, independently:

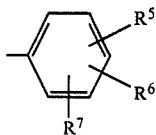 (a)

(b) hydrogen, or a primary or secondary $C_{1-6}$alkyl not containing an asymmetric carbon atom, (c) $C_{3-6}$cycloalkyl or (d) phenyl-$(CH_2)_m$-, wherein $R^5$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy;

$R^6$ is hydrogen, $C_{1-3}$alkyl, $C_{1-3}$alkoxy, fluoro or chloro;

$R^7$ is hydrogen, $C_{1-2}$alkyl, $C_{1-2}$alkoxy, fluoro or chloro;

m is 1, 2 or 3;

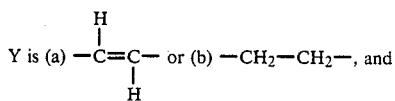

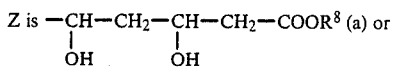

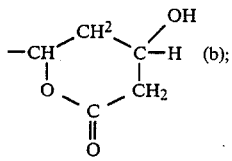

in which $R^8$ is hydrogen, $R^9$ or M, wherein $R^9$ is a physiologically acceptable and hydrolyzable ester group, and M is a pharmaceutically acceptable cation.

2. A compound of claim 1 in which Y is of type (a).
3. A compound of claim 2 in which $R^1$ is of type (a).
4. A compound of claim 3 in which $R^2$ is a primary alkyl.
5. A compound of claim 2 in which $R^2$ is isopropyl.
6. A compound of claim 1 in which $R^8$ is hydrogen.
7. A compound of claim 1 in which $R^8$ is a physiologically acceptable and hydrolyzable ester group.
8. A compound of claim 1 in which $R^8$ is a pharmaceutically acceptable cation.
9. A compound of claim 1 in which $R^1$ is isopropyl.
10. A compound of claim 1 in which $R^2$ is hydrogen.
11. A compound of claim 2, in which $R^2$ is of type (a).
12. A compound of claim 5 which is ethyl 7-[3-(4-fluorophenyl)1-isopropyl-2-indolizinyl-3,5-dihydroxy-6-heptenoate (trans).
13. A compound of claim 10 which is ethyl 7-[3-(4-fluorophenyl)-2-indolizinyl-3,5-dihydroxy-6-hept-enoate (trans).
14. A compound of claim 11 which is ethyl 7-[1-(4-fluorophenyl)-3-isopropyl-2-indolizinyl-3,5-dihydroxy-6-hept-enoate (trans).
15. A compound of claim 5 which is sodium 7-[3-(4-fluorophenyl)1-isopropyl-2-indolizinyl-3,5-dihydroxy-6-hept-enoate (trans).
16. A compound of claim 10 which is sodium 7-[3-(4-fluorophenyl)-2-indolizinyl-3,5-dihydroxy-6-hept-enoate (trans).
17. A compound of claim 11 which is sodium 7-[1-(4-fluorophenyl)-3-isopropyl-2-indolizinyl-3,5-dihydroxy-6-hept-enoate (trans).
18. A composition useful for treating atherosclerosis in a mammal in need of such treatment, comprising an effective amount of a compound of claim 1 and an inert non-toxic, pharmaceutically acceptable carrier, the amount of compound being an amount effective for inhibiting cholesterol biosynthesis in a mammal.
19. A method of treating atherosclerosis by inhibiting cholesterol biosynthesis comprising administering to a mammal in need of such treatment an amount effective for inhibiting cholesterol biosynthesis of a compound of claim 1.
20. A compound of claim 15 in the erythro form.

* * * * *